(12) United States Patent  
Gilkerson et al.

(10) Patent No.: US 7,606,620 B2  
(45) Date of Patent: *Oct. 20, 2009

(54) SYSTEM AND METHOD FOR DETECTION ENHANCEMENT PROGRAMMING

(75) Inventors: James O. Gilkerson, Stillwater, MN (US); Vickie L. Conley, Woodbury, MN (US); Scott Stubbs, Maple Grove, MN (US); Douglas J. Lang, Arden Hills, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 572 days.

This patent is subject to a terminal disclaimer.

(21) Appl. No.: 11/369,142

(22) Filed: Mar. 6, 2006

(65) Prior Publication Data

US 2006/0167520 A1    Jul. 27, 2006

Related U.S. Application Data

(63) Continuation of application No. 10/339,926, filed on Jan. 10, 2003, now abandoned, which is a continuation of application No. 09/569,928, filed on May 13, 2000, now Pat. No. 6,522,925.

(51) Int. Cl.  
*A61N 1/00* (2006.01)

(52) U.S. Cl. .............. 607/30; 607/32; 607/59

(58) Field of Classification Search ............... 607/4–28, 607/30–32, 59, 60  
See application file for complete search history.

(56) References Cited

U.S. PATENT DOCUMENTS

| | | | |
|---|---|---|---|
| 4,549,552 A | 10/1985 | Groch et al. | |
| 4,680,708 A | 7/1987 | Ambos et al. | |
| 5,002,052 A | 3/1991 | Haluska | |
| 5,047,930 A | 9/1991 | Martens et al. | |
| 5,113,869 A | 5/1992 | Nappholz et al. | |
| 5,127,401 A | 7/1992 | Grevious et al. | |
| 5,161,527 A | 11/1992 | Nappholz et al. | |
| 5,299,118 A | 3/1994 | Martens et al. | |
| 5,312,448 A | 5/1994 | Hognelid et al. | |
| 5,341,811 A | 8/1994 | Cano | |
| 5,360,437 A | 11/1994 | Thompson | |

(Continued)

FOREIGN PATENT DOCUMENTS

EP          253505 A2      1/1988

(Continued)

OTHER PUBLICATIONS

"Pacemaker System Guide for Pulsar Max II; Mulitprogrammable Pacemakers", Product brochure published by Guidant Corporation,(Apr. 18, 1999), pp. 6-48 and 6-49.

(Continued)

*Primary Examiner*—Scott M Getzow  
(74) *Attorney, Agent, or Firm*—Schwegman, Lundberg & Woessner, P.A.

(57) ABSTRACT

A system and method of enabling detection enhancements selected from a plurality of detection enhancements. In a system having a plurality of clinical rhythms, including a first clinical rhythm, where each of the detection enhancements is associated with the clinical rhythms, the first clinical rhythm is selected. The first clinical rhythm is associated with first and second detection enhancements. When the first clinical rhythm is selected, parameters of the first and second detection enhancements are set automatically. A determination is made as to whether changes are to be made to the parameters. If so, one or more of the parameters are modified under user control.

20 Claims, 17 Drawing Sheets

U.S. PATENT DOCUMENTS

| | | | |
|---|---|---|---|
| 5,366,487 | A | 11/1994 | Adams et al. |
| 5,379,776 | A | 1/1995 | Murphy et al. |
| 5,411,528 | A | 5/1995 | Miller et al. |
| 5,433,198 | A | 7/1995 | Desai |
| 5,480,422 | A | 1/1996 | Ben-Haim |
| 5,487,755 | A | 1/1996 | Snell et al. |
| 5,513,645 | A | 5/1996 | Jacobson et al. |
| 5,549,654 | A | 8/1996 | Powell |
| 5,607,460 | A | 3/1997 | Kroll et al. |
| 5,620,471 | A | 4/1997 | Duncan |
| 5,620,472 | A | 4/1997 | Rahbari |
| 5,643,255 | A | 7/1997 | Organ |
| 5,683,431 | A | 11/1997 | Wang |
| 5,716,384 | A | 2/1998 | Snell |
| 5,725,559 | A | 3/1998 | Alt et al. |
| 5,803,084 | A | 9/1998 | Olson |
| 5,833,623 | A | 11/1998 | Mann et al. |
| 5,891,170 | A | 4/1999 | Nitzsche et al. |
| 5,961,467 | A | 10/1999 | Shimazu et al. |
| 6,014,581 | A | 1/2000 | Whayne et al. |
| 6,017,307 | A | 1/2000 | Raines |
| 6,088,618 | A | 7/2000 | Kerver |
| 6,108,578 | A | 8/2000 | Bardy et al. |
| 6,134,469 | A | 10/2000 | Wietholt |
| 6,151,524 | A | 11/2000 | Krig et al. |
| 6,178,350 | B1 | 1/2001 | Olson et al. |
| 6,230,055 | B1 | 5/2001 | Sun et al. |
| 6,240,317 | B1 | 5/2001 | Villaseca et al. |
| 6,253,102 | B1 | 6/2001 | Hsu et al. |
| 6,289,248 | B1 | 9/2001 | Conley et al. |
| 6,317,632 | B1 | 11/2001 | Krig et al. |
| 6,321,117 | B1 | 11/2001 | Koshiol et al. |
| 6,400,981 | B1 | 6/2002 | Govari |
| 6,415,175 | B1 | 7/2002 | Conley et al. |
| 6,445,952 | B1 | 9/2002 | Manrodt et al. |
| 6,493,579 | B1 | 12/2002 | Gilkerson et al. |
| 6,522,925 | B1 | 2/2003 | Gilkerson et al. |
| 6,658,286 | B2 | 12/2003 | Seim |
| 6,671,548 | B1 | 12/2003 | Mouchawar et al. |
| 7,010,349 | B2 | 3/2006 | Conley et al. |
| 2002/0147407 | A1 | 10/2002 | Seim |
| 2003/0105491 | A1 | 6/2003 | Gilkerson et al. |
| 2005/0038480 | A1 | 2/2005 | Ding |

FOREIGN PATENT DOCUMENTS

| | | | |
|---|---|---|---|
| EP | 0360412 | A1 | 3/1990 |
| EP | 360412 | A2 | 3/1990 |
| EP | 0401962 | A1 | 12/1990 |
| EP | 469817 | A2 | 2/1992 |
| EP | 0597459 | A2 | 5/1994 |
| EP | 597459 | A2 | 5/1994 |
| EP | 0617980 | A2 | 10/1994 |
| EP | 744190 | A2 | 11/1996 |
| EP | 0748638 | A2 | 12/1996 |
| EP | 919256 | A2 | 6/1999 |
| EP | 993842 | A1 | 4/2000 |
| EP | 1112756 | A2 | 7/2001 |
| WO | WO-9302746 | A1 | 2/1993 |
| WO | WO-9739798 | A1 | 10/1997 |
| WO | WO-9739799 | A1 | 10/1997 |
| WO | WO-9825669 | A1 | 6/1998 |
| WO | WO-9848891 | A1 | 11/1998 |
| WO | WO-9915232 | A1 | 4/1999 |
| WO | WO-0053089 | A1 | 9/2000 |
| WO | WO-0059573 | A1 | 10/2000 |
| WO | WO-0113993 | A1 | 3/2001 |
| WO | WO-03047690 | A2 | 6/2003 |
| WO | WO 2006049767 | A1 | 5/2006 |

OTHER PUBLICATIONS

"Screenshots taken of Display of Model 2920 Programmer, Using Model 2845 Software Application", *Guidant Corporation*, Effective Date of First Use: Dec. 2, 1999. See e-mail in matter management in 279.562US1 or 279.202US3., 5 pgs.

Lovett, Eric , "Cardiac Pacing System for Prevention of Ventricular Fibrillation and Ventricular Tachycardia Episode", U.S. Appl. No. 09/569,295, filed May 13, 2000, 71 pgs.

Medtronic, "Marquis DR 7274 Dual Chamber Implantable Cardioverter Defibrillator", Reference Manual,(Feb. 2002), 426 pgs.

Zhang, Yi , "Methods and Apparatuses for Arrhythmia Detection and Classification Using Wireless ECG", U.S. Appl. No. 10/975,166, filed Oct. 28, 2004, 69 pgs.

Zhu, D., et al., "Pacing Therapy for Atrial Tachyarrhythmias", *Clin. Cardiol.* vol. 19, (Sep. 1996), pp. 737-742.

"U.S. Appl. No. 09/378,029, Non-Final Office Action mailed Mar. 28, 2001", 4 pgs.

"U.S. Appl. No. 09/378,029, Response filed Jun. 28, 2001 to Non-Final Office Action mailed Mar. 28, 2001", 8 pgs.

"U.S. Appl. No. 10/025,958, Non-Final Office Action mailed Jan. 8, 2008", 11 pgs.

"U.S. Appl. No. 10/025,958, Response filed Mar 8, 2008 to Non-Final Office Action mailed Jan. 8, 2008", 15 pgs.

"U.S. Appl. No. 10/025,958, Response filed Oct. 30, 2007 to Final Office Action mailed Oct. 15, 2007", 17 pgs.

"U.S. Appl. No. 10/025,958, Response filed Dec. 3, 2008 to Final Office Action mailed Sep. 3, 2008", 18 pgs.

"U.S. Appl. No. 10/025,958 Final Office Action Mailed Oct. 15, 2007", 12 pgs.

"U.S. Appl. No. 10/025,958 Final Office Action mailed Sep. 3, 2008.", 11 pgs.

|  | VT-1 ZONE | VT ZONE | VF ZONE |
|---|---|---|---|
| 1-ZONE CONFIGURATION |  |  | NONE |
| 2-ZONE CONFIGURATION |  | V RATE > A RATE<br>AFIB RATE THRESHOLD<br>STABILITY<br>ONSET<br>SRD<br>SHOCK IF UNSTABLE [a] | NONE |
| 3-ZONE CONFIGURATION | V RATE > A RATE<br>AFIB RATE THRESHOLD<br>STABILITY<br>ONSET<br>SRD | SHOCK IF UNSTABLE | NONE | a. SHOCK IF UNSTABLE CANNOT BE PROGRAMMED ON IN THE SAME ZONE AS OTHER DETECTION ENHANCEMENTS THAT ARE PROGRAMMED TO INHIBIT THERAPY (ONSET, STABILITY, AND AFIB RATE THRESHOLD)

FIG. 5

| DETECTED RHYTHM | AFIB RATE THRESHOLD WITH STABILITY |
|---|---|
| GRADUAL, UNSTABLE<br>A > AFIB RATE THRESHOLD | INHIBIT UNTIL V > A OR SRD (IF ON) |
| GRADUAL, UNSTABLE<br>A < AFIB RATE THRESHOLD | INHIBIT UNTIL V > A OR SRD (IF ON) |
| SUDDEN, UNSTABLE<br>A > AFIB RATE THRESHOLD | INHIBIT UNTIL STABLE, V > A OR SRD (IF ON) |
| SUDDEN, UNSTABLE<br>A < AFIB RATE THRESHOLD | TREAT IMMEDIATELY AT END OF DURATION [a] |
| GRADUAL, STABLE<br>A > AFIB RATE THRESHOLD | TREAT IMMEDIATELY AT END OF DURATION [b] |
| GRADUAL, STABLE<br>A < AFIB RATE THRESHOLD | INHIBIT UNTIL V > A OR SRD (IF ON) |
| SUDDEN, STABLE<br>A > AFIB RATE THRESHOLD | TREAT IMMEDIATELY AT END OF DURATION |
| SUDDEN, STABLE<br>A < AFIB RATE THRESHOLD | TREAT IMMEDIATELY AT END OF DURATION | a. IF V RATE > A RATE IS PROGRAMMED ON AND IS FALSE, THEN THERAPY WILL BE INHIBITED IF THE RHYTHM IS UNSTABLE b. IF V RATE > A RATE IS PROGRAMMED ON AND IS FALSE, THERAPY WILL STILL BE INITIATED BECAUSE THE RHYTHM IS DECLARED STABLE

FIG. 7

| DETECTED RHYTHM | POSSIBLE COMBINATIONS | POSSIBLE COMBINATIONS | POSSIBLE COMBINATIONS |
| --- | --- | --- | --- |
| GRADUAL, UNSTABLE | ONSET AND STABILITY[a] | INHIBIT UNTIL V > A OR SRD (IF ON) | ONSET OR STABILITY |
| GRADUAL, STABLE | INHIBIT UNTIL V > A OR SRD (IF ON) | INHIBIT UNTIL V > A OR SRD (IF ON) | INHIBIT UNTIL RHYTHM BECOMES STABLE, V > A, OR SRD (IF ON) |
| SUDDEN, UNSTABLE | INHIBIT UNTIL RHYTHM BECOMES STABLE, OR V > A, OR SRD (IF ON) | | TREAT IMMEDIATELY AT END OF DURATION |
| SUDDEN, STABLE | TREAT IMMEDIATELY AT END OF DURATION | | TREAT IMMEDIATELY AT END OF DURATION |
| | | | TREAT IMMEDIATELY AT END OF DURATION | a. THE AND COMBINATION IS THE NOMINAL SETTING WHEN BOTH ARE ENABLED

FIG. 8

VT-1 Detection Enhancements

Initial

| | Present | Change | |
|---|---|---|---|
| V Rate > A Rate | On | | |
| A Fib Rate Threshold | Off | | bpm |
| Stability | 10 | | ms |
| And | | Or | |
| Onset | 9% | | % |
| Sustained Rate Duration | 0:30 | | m:s |

Redetection

| | Present | Change | |
|---|---|---|---|
| Post-Shock | | | |
| V Rate > A Rate | On | | |
| A Fib Rate Threshold | 10 | | bpm |
| Stability | 9 | | ms |
| Sustained Rate Duration | 0:30 | | m:s |

(Cancel Changes) (Close)

| | RHYTHM DISCRIMINATION AVAILABLE PER ZONE | | |
| --- | --- | --- | --- |
| | VT-1 ZONE | VT ZONE | VF ZONE |
| 3-ZONE CONFIGURATION | ATRIAL TACHYARRHYTHMIA SINUS TACHYCARDIA | POLYMORPHIC VT | NONE |
| 2-ZONE CONFIGURATION | | ATRIAL TACHYARRHYTHMIA SINUS TACHYCARDIA OR POLYMORPHIC VT | NONE |

FIG. 11

| PARAMETER | ATRIAL TACHYARRHYTHMIA | SINUS TACHYCARDIA | POLYMORPHIC VT |
|---|---|---|---|
| V > A | ON | ON | |
| A FIB RATE THRESHOLD | 200 MIN$^{-1}$ | | |
| STABILITY (INHIBIT) | 10 ms | | |
| ONSET (INITIAL DETECTION ONLY) | | 9 % | |
| SRD    INITIAL<br>REDETECTION | 0:30 MINUTES:SECONDS<br>0:15 MINUTES:SECONDS | 0:30 MINUTES:SECONDS | |
| SHOCK IF UNSTABLE | | | 30 MS |

FIG. 12

| PARAMETER | ATRIAL TACHYARRHYTHMIA | SINUS TACHYCARDIA | POLYMORPHIC VT |
|---|---|---|---|
| STABILITY (INHIBIT) | 30 ms | | |
| ONSET (INITIAL DETECTION ONLY) | | 9 % | |
| SRD     INITIAL<br>REDETECTION | 0:30 MINUTES:SECONDS<br>0:15 MINUTES:SECONDS | 0:30 MINUTES:SECONDS | |
| SHOCK IF UNSTABLE | | | 30 MS |

FIG. 13

VT-1 Detection

| Initial | Present | Change | | Redetection | Present | Change | |
|---|---|---|---|---|---|---|---|
| Rate | 160 | 145 | bpm | Redetection Duration | 1.0 | | sec |
| Interval | 375 | 415 | ms | Post-shock Duration | 1.0 | | sec |
| Duration | 2.5 | | sec | | | | |

Present Change
   On

🔍 Detection Enhancements
☑ Atrial Tachyarrhythmia Discrimination
☑ Sinus Tachycardia Discrimination ( Cancel Changes )

FIG. 14

SYSTEM AND METHOD FOR DETECTION ENHANCEMENT PROGRAMMING

CROSS-REFERENCE TO RELATED APPLICATION

This application is a continuation of U.S. application Ser. No. 10/339,926, filed on Jan. 10, 2003, now abandoned, which is a continuation of U.S. application Ser. No. 09/569,928, filed on May 13, 2000, now issued as U.S. Pat. No. 6,522,925, the specifications of which are incorporated by reference herein.

FIELD OF THE INVENTION

The present invention is related to implantable cardioverter defibrillator therapy, and more particularly to a system and method for displaying and selecting detection enhancements within a cardioverter defibrillator.

BACKGROUND INFORMATION

Detection enhancements are used in implantable cardioverter defibrillator therapy to reduce the incidence of inappropriate shocks. In the past, defibrillators were only rate derivative. If the patient's heart rate crossed over the prescribed rate, a shock was delivered to the heart. Experience showed that the heart could pass through the prescribed rate for a variety of reasons, only some of which warranted shocking the heart. For instance, the heart could beat faster during exercise, or because the person was excited, or even due to atrial arrhythmia. None of these warrant shock therapy.

Detection enhancements are sets of rules for determining when to deliver shock therapy. These rules may, for instance, look not only at the change in rate but also at the source of the arrhythmia, at the suddenness of onset or at the stability of the heart beat.

In the past, detection enhancements were treated as separate items on a laundry list of possible detection enhancements. The language used to describe the features was often a reflection of the programming code used to implement the features. Such an approach was confusing to physicians. As a result, physicians either ignored the enhancements or struggled with programming the detection enhancements into the patient's defibrillator.

What is needed is a system and method for displaying and selecting detection enhancements within a cardioverter defibrillator which addresses these deficiencies.

SUMMARY OF THE INVENTION

According to one aspect of the present invention, a system and method of enabling detection enhancements selected from a plurality of detection enhancements is described. In a system having a plurality of clinical rhythms, including a first clinical rhythm, where each of the detection enhancements is associated with the clinical rhythms, the first clinical rhythm is selected. The first clinical rhythm is associated with first and second detection enhancements. When the first clinical rhythm is selected, parameters of the first and second detection enhancements are set automatically. A determination is made as to whether changes are to be made to the parameters. If so, one or more of the parameters are modified under user control.

According to another aspect of the present invention, a system and method of programming one or more detection enhancements into a defibrillator is described. In a system having a plurality of clinical rhythms, including a first clinical rhythm, where each of the detection enhancements is associated with the clinical rhythms, the first clinical rhythm is selected. The first clinical rhythm is associated with first and second detection enhancements. When the first clinical rhythm is selected, parameters of the first and second detection enhancements are set automatically. A determination is made as to whether changes are to be made to the parameters. If so, one or more of the parameters are modified under user control. The defibrillator is then programmed to perform the first and second detection enhancements as a function of the parameters.

BRIEF DESCRIPTION OF THE DRAWINGS

In the drawings, where like numerals refer to like components throughout the several views:

FIG. 5 illustrates detection enhancements availability within zones of a multi-zone configuration;

FIG. 7 illustrates representative Onset, Stability and AFib Rate combinations and the suggested therapy;

FIG. 8 illustrates representative Onset and Stability combinations and the suggested therapy;

FIG. 10 illustrates detection enhancement details for VT-1 zone;

FIG. 11 illustrates rhythm discrimination available per zone in multi-zone configurations;

FIGS. 12 and 13 illustrate one embodiment of pre-selected parameter values suitable for detection enhancements by clinical rhythm;

FIG. 14 illustrates detection enhancement details for VT-1 zone;

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural changes may be made without departing from the scope of the present invention.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Figure 1:
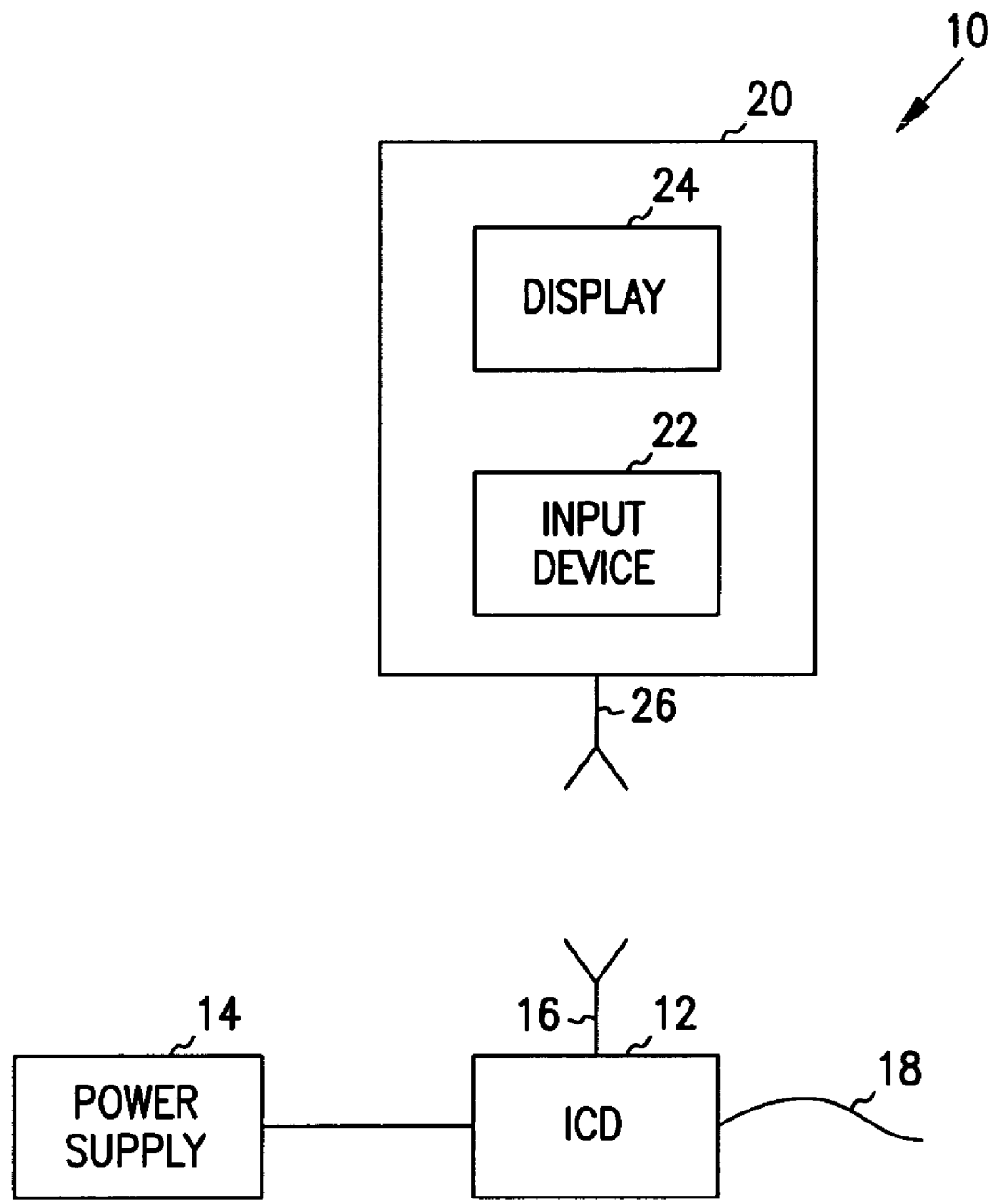
FIG. 1 illustrates an implantable cardioverter defibrillator within a shock therapy system.

FIG. 1 illustrates an implantable shock therapy system. Shock therapy system 10 includes a defibrillator 12, a power supply 14 and a programmer 20. Power supply 14 is connected to defibrillator 12 and supplies power to defibrillator 12.

In one such embodiment, defibrillator 12 includes a telemetry system 16 for communicating with programmer 20. In addition, defibrillator 12 supplies the requisite therapy to the heart via leads 18.

In one embodiment, programmer 20 includes an input device 22 such as a keyboard or mouse, a display 24 and telemetry system 26. Features selected or programmed by physicians into programmer 20 are communicated through telemetry to defibrillator 12, where they control shock and pacing therapy applied to the patient's heart. Detection enhancements are just some of the features programmed in this manner by the physician.

As noted above, in the past detection enhancements were treated as separate items on a laundry list of possible detection enhancements. The language used to describe the features was often a reflection of the programming code used to implement the features. Such an approach was confusing to physicians. As a result, physicians either ignored the enhancements or struggled while programming the detection enhancements into the patient's defibrillator.

As a response to this problem, programmer 20 includes control logic which allows the physician to program all appropriate enhancements by a process of selection. In one embodiment, the physician checks boxes that describe the patient's arrhythmia (e.g., Atrial Fibrillation or Sinus Tachycardia). In another embodiment, symbols representative of the arrhythmia are displayed to be selected by the user. For instance, if there are two detection enhancements that protect against sinus tachycardia, a symbol labeled "sinus tachycardia protection" is displayed.

In one embodiment, the physician uses input device 22 to indicate the selected arrhythmia and programmer 20 programs defibrillator 12 to perform the underlying detection enhancements. In one such embodiment, programmer 20 uses artificial intelligence to set values of parameters within each of the desired detection enhancements. These values may be default values, or can be calculated as a function of patient or therapy parameters already established in programmer 20. In one expert system embodiment, a set of rules establish the values set for parameters programmed automatically by programmer 20. Such a system is described below.

A system which programs detection enhancements by simply checking clinical rhythms and letting the programmer do the rest may not be flexible enough to meet the varying demands of the real world. To address this, in one embodiment, programmer 20 includes control logic which allows the physician to manipulate parameters associated with the detection enhancements selected on the basis of clinical rhythms. This provides the experienced physician the ability to manipulate the values of parameters associated with particular detection parameters, while letting the less sophisticated user rely on the expertise of the engineers and physicians who designed the defibrillator system.

Figure 2:
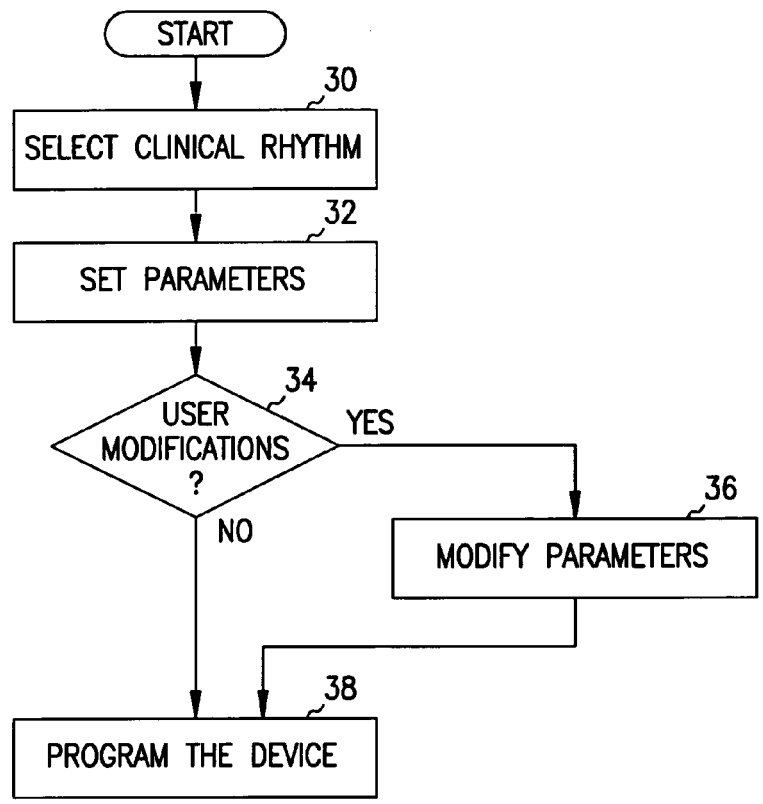
FIG. 2 illustrates a method of selecting detection enhancements from a plurality of possible detection enhancements and of modifying parameters associated with the selected detection enhancements.

One method of selecting detection enhancements from a plurality of possible detection enhancements and of modifying parameters associated with the selected detection enhancements is shown in FIG. 2. Programmer 20 is programmed to include a number of different clinical rhythms. Each clinical rhythm is associated with one or more detection enhancements. At 30, the physician selects one or more of the available clinical rhythms. In one embodiment, programmer 20 displays the available clinical rhythms on display 24 so that the physician can select one or more clinical rhythms through input device 22. In another embodiment, the physician may enter the desired clinical rhythms by typing or dictating labels corresponding to the desired rhythm into input device 22.

Once the one or more clinical rhythms has been selected, control moves to 32, where programmer 20 identifies the detection enhancements associated with the selected clinical rhythms and sets parameters associated with the identified detection enhancements. Control moves to 34, where a determination is made as to whether the physician wishes to modify one or more of the detection enhancement parameters. This may be done, for example, by directly querying the physician on display 22, or by presenting a set of options which includes a "Modify parameters" button or icon.

If a determination is made that the physician does not wish to modify one or more of the detection enhancement parameters, control moves to 38, where the detection enhancement parameters are programmed into defibrillator 12.

If a determination is made that the physician does wish to modify one or more of the detection enhancement parameters, control moves to 36, and the physician enters or modifies the desired values. Control then moves to the 38, where the detection enhancement parameters are programmed into defibrillator 12.

Figure 3:
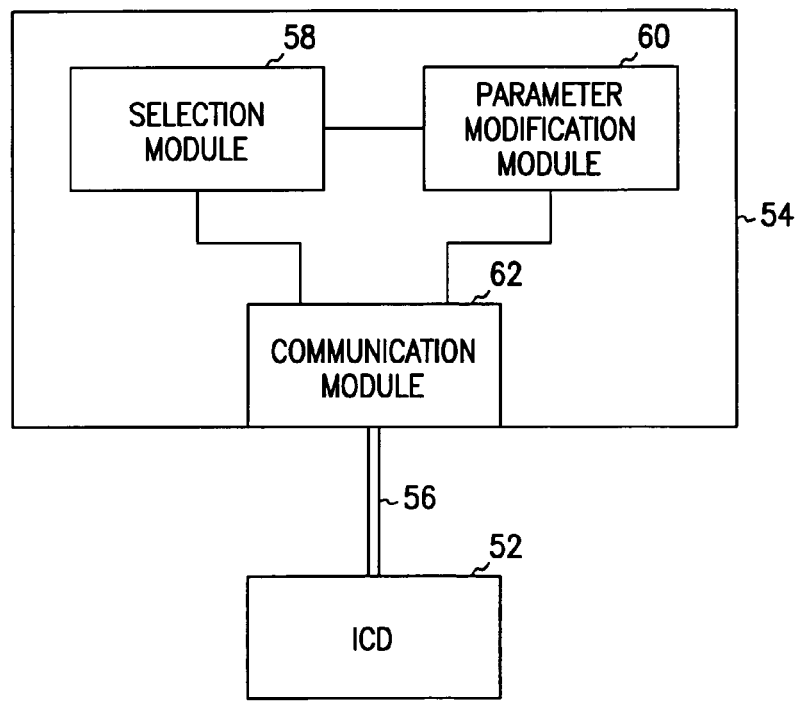
FIG. 3 illustrates one embodiment of the system of FIG. 1.

One embodiment of a system 10 used to deliver shock therapy to a heart is shown in FIG. 3. In FIG. 3, shock therapy system 50 includes a defibrillator 52, a programmer 54 and a communications link 56. Communications link 56 transfers data between defibrillator 52 and programmer 54. Embodiments of communications link 56 include wired, wireless, optical and other forms of communications.

In one such embodiment, programmer 54 includes selection module 58, parameter modification module 60 and communication module 62. Selection module 58 displays the available clinical rhythms. Each clinical rhythm is associated with one or more detection enhancements. Selection module 58 also includes a user interface which allows a user to select one or more to the clinical rhythms.

Parameter modification module 60 receives the selected clinical rhythm from first control logic 58, stores parameters related to the associated detection enhancements, determines if the user wishes to modify the parameters, and, if the user modifies the parameters, stores the modified parameters.

Communication module 62 programs defibrillator 52 to perform the associated detection enhancements as a function of the stored parameters. Module 62 also is connected to selection module 58 in order to display data captured by defibrillator 52.

In one embodiment, a user interface is designed for system 10 to provide a "layering" effect. That is, the top screen is designed to provide easy activation of the detection enhancements by displaying clinical rhythm discrimination features that the physician may wish to program. Parameters associated with the selected detection enhancements are seeded with a suggested set of nominal values; the physician can choose to accept these values or can change any or all values as desired. If the physician chooses to change the suggested values, access is given to an underlying screen where the specific detection enhancements are listed, and the programming values are accessible. With this dual-layer approach, system 10 provides the flexibility to the physician to either use proven, preselected values or to change the values to patient specific settings.

As noted above, detection enhancements are used to add specificity to rate and duration detection criteria. In one embodiment, enhancements can be programmed to delay or inhibit therapy, to bypass therapy inhibition, or to bypass a sequence of ATP therapy in favor of shock therapy. Some of the available detection enhancements include V Rate>A Rate, AFib Rate Threshold, Stability, Onset, Shock if Unstable and Sustained Rate Duration (SRD).

The V Rate>A Rate enhancement is used to deliver therapy anytime the ventricular rate is greater than the atrial rate. It can also be used to bypass the Onset, Stability, and/or AFib Rate Threshold parameters' decision to inhibit therapy.

The AFib Rate Threshold enhancement is programmed to inhibit ventricular therapy if the atrial rhythm is fast. The Stability parameter is programmed to inhibit therapy delivery if the ventricular rhythm is unstable. Onset is programmed to inhibit therapy if the patient's heart rate increases gradually. The Shock if Unstable parameter is programmed to bypass ATP therapy and deliver shock therapy if the analysis of the ventricular rhythm is declared to be unstable. The Sustained Rate Duration (SRD) parameter enables the pulse generator to override the Onset, Stability, or AFib Rate Threshold parameters' decision to inhibit therapy if the high rate continues throughout the programmed time period.

In one embodiment, if any of the following features, V Rate>A Rate, AFib Rate Threshold, Brady Mode programmed to DDD(R), DDI(R), DVI(R), VDD(R), or AAI(R), Electrogram Storage Enabled for the atrial electrode, or Atrial Rate EGM trace selected are programmed, the pulse generator will respond to atrial sensing whether an atrial lead is implanted or not. If an atrial lead is not implanted, atrial data will be erroneous.

The atrial rate may be used to both 1) inhibit therapy in the presence of atrial fibrillation (AFib) or atrial flutter, and 2) to bypass Onset, Stability, and/or AFib Rate Threshold as inhibitors if programmed On and the ventricular rate is faster than the atrial rate.

The V Rate>A Rate (ventricular rate greater than atrial rate) parameter can be programmed to bypass inhibitors (Onset, Stability, and/or AFib Rate Threshold) and initiate therapy in the event that the ventricular rate is faster than the atrial rate. It can be programmed On or Off. Analysis is made by comparing the average rate of the last 10 ventricular intervals prior to the end of duration to the average rate of the last 10 atrial intervals prior to the end of duration and after the third fast ventricular interval. If fewer than 10 atrial intervals are available, then the intervals available will be used to calculate the average atrial rate. If the average ventricular rate is greater than the average atrial rate by at least 10 min$^{-1}$, the ventricular rate is declared to be faster than the atrial rate (indicated as True on the Episode Detail report) and therapy will be initiated. If the ventricular rate is not greater than the atrial rate (indicated as False on the Episode Detail report), then therapy may continue to be inhibited.

If therapy is inhibited, the V Rate>A Rate analysis continues until either the ventricular rate is greater than the atrial rate or the other enhancements indicate therapy treatment, at which time therapy will be initiated.

Atrial rate detection is used to inhibit therapy in the event that the underlying cause of a moderately high ventricular rate is due to ventricular response to fibrillation in the atrium. This is accomplished by comparing the atrial rate to the preprogrammed AFib Rate Threshold. If the atrial rate is greater than the AFib Rate Threshold, therapy will be withheld until the atrial rate drops below the AFib Rate Threshold, or, if programmed On, the V Rate>A Rate is True, or the Sustained Rate Duration timer expires. Programmable values for the AFib Rate Threshold are Off or 200-400 min$^{-1}$.

When the AFib Rate Threshold is programmed separately from the Stability parameter, a determination is made that the atrial rate is above the AFib Rate Threshold in the following manner. At initiation of ventricular tachyarrhythmia detection, atrial analysis begins. Each atrial interval is classified as faster or slower than the AFib Rate Threshold interval. When 6 of the last 10 intervals are classified as faster than the AFib Rate Threshold, the device declares atrial fibrillation to be present. Therapy will be withheld, and the atrial rate will continue to be examined; as long as 4 of 10 intervals remain classified as fast, atrial fibrillation continues to be present. When programmed with Stability the ventricular rhythm is also considered in the decision.

If AFib Rate Threshold and Stability are both programmed On, the device will analyze both parameters to determine if therapy is to be delivered or withheld. If the atrial rate is greater than the AFib Rate Threshold and the ventricular rhythm is classified as unstable, the ventricular rhythm is declared to be due to atrial fibrillation.

Figure 6:
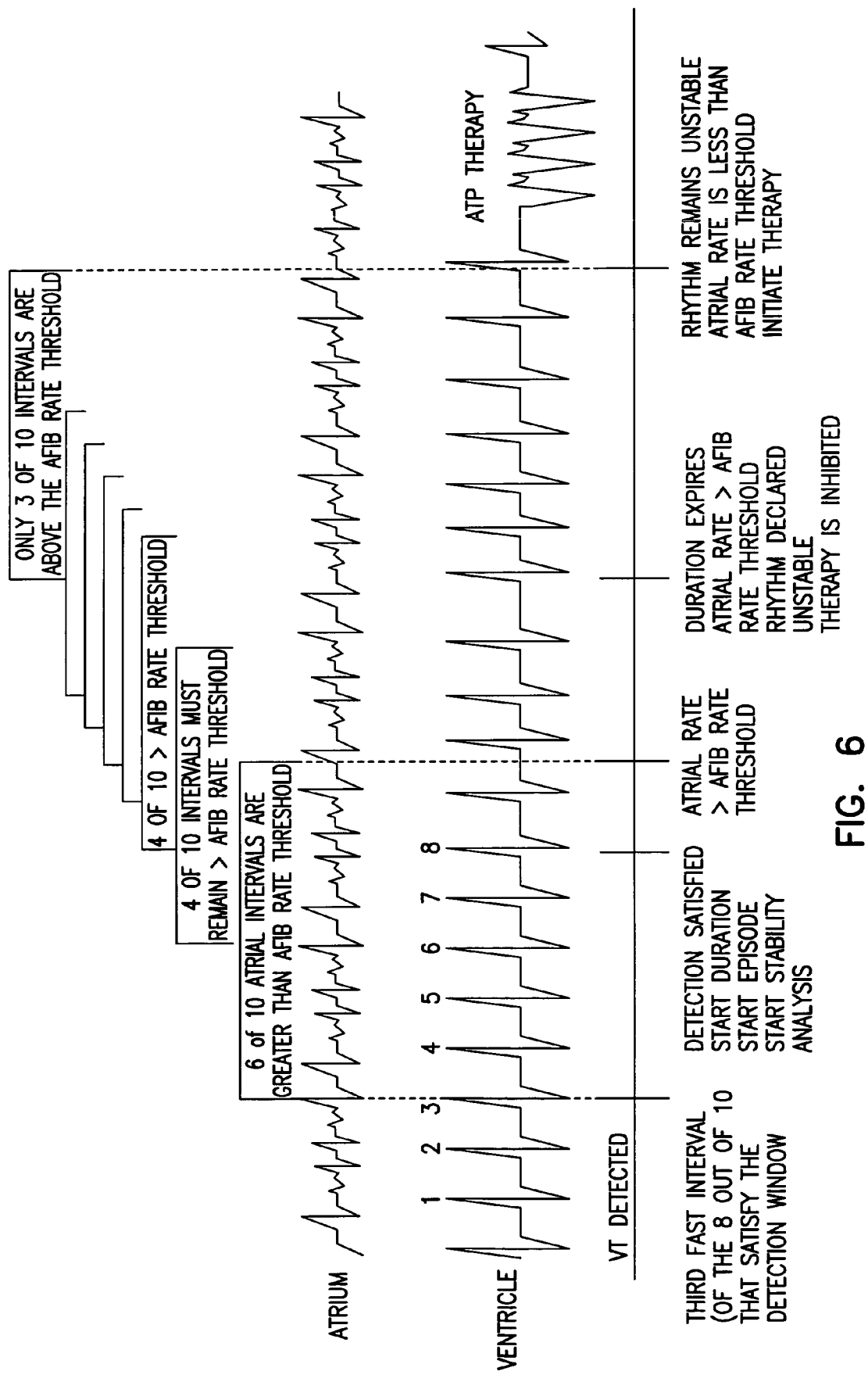
FIG. 6 illustrates AFib Rate Threshold and Stability interaction.

The atrial rate is declared to be above the AFib Rate Threshold in the manner discussed above. Ventricular stability is then checked and, if unstable, therapy will be inhibited. In the event that therapy is not delivered, the atrial rate will continue to be examined; as long as 4 of 10 intervals remain classified as fast, atrial fibrillation continues to be present. Therapy is inhibited until the atrial rate drops below the AFib Rate Threshold, the ventricular rhythm becomes stable, or if programmed On, V Rate>A Rate is true or Sustained Rate Duration times out. An illustration of AFib Rate Threshold and Stability interaction is shown in FIG. 6.

In one embodiment, the device will initiate therapy when a stable rhythm is declared; and will initiate therapy for an unstable rhythm when it is determined that the atrial rate is less than the AFib Rate Threshold.

If the AFib Rate Threshold, Stability, and Onset parameters are all programmed On, to initiate therapy the rhythm must have a sudden onset and either the ventricular rate must be stable or the atrial rate must be less than the AFib Rate Threshold. If the detection enhancement V Rate>A Rate is programmed On and is determined to be True, it takes precedence over all other inhibitor enhancements.

The Onset enhancement measures the rate of transition in ventricular rhythm from slow rates to tachycardia. It is intended to differentiate physiologic sinus tachycardias, which typically begin slowly, from pathologic tachycardias, which typically begin abruptly. With Onset enabled, the device inhibits therapy in the lowest tachycardia rate zone if the rate increase is gradual. Programmable values for Onset are Off or 9-50% or 50-250 ms.

The Onset enhancement is measured using ventricular rate only and may be programmed as a percentage of cycle length, or as an interval length in ms. It is limited to the lowest zone of a multizone configuration. The selected Onset value represents the minimum difference that must exist between intervals that are below the lowest programmed rate threshold and intervals that are above the lowest programmed rate threshold. The pulse generator performs Onset calculations (even when it is programmed Off) for all episodes except induced episodes, and stores the measured Onset results from a two-stage calculation in therapy history. This stored data (in ms and %) is useful in programming an appropriate Onset value.

When a detection window becomes satisfied (episode declared and memory allotted for history data storage), the pulse generator begins calculating for sudden onset in a two-stage sequence.

The first stage measures the intervals prior to the start of the episode and locates the pair of adjacent intervals (pivot point) where the cycle length decreased the most. If the decrease in cycle length is equal to or greater than the programmed Onset value, the first stage declares onset to be sudden.

The second stage then compares additional intervals; if the difference between the average interval before the pivot point and 3 out of the first 4 intervals following the pivot point is equal to or greater than the programmed Onset threshold, the second stage declares onset to be sudden.

If both stages declare the rhythm sudden, therapy will be initiated. If either stage indicates a gradual onset, initial therapy will be inhibited in the lowest zone; then therapy will be delivered only if the rate accelerates to a higher zone, information from the atrial lead determines that the ventricular rate is faster than the atrial rate (V Rate>A Rate programmed On), or the Sustained Rate Duration (SRD) timer expires.

Stability analysis is used to distinguish unstable (irregular) ventricular rhythms from stable (regular) ventricular rhythms. This is accomplished by measuring the degree of variability of the tachycardia R-R intervals. This degree of variability, when used by itself, may allow the device to distinguish conducted atrial fibrillation (which may produce greater R-R variability) from monomorphic VT (which is typically stable). It also may be used to differentiate MVTs (which are pace terminable) from polymorphic VTs and VF (which are typically not pace terminable). Based on the patient's needs, the physician may choose to program Stability as an inhibitor to prevent therapy for atrial fibrillation, or use stability analysis to direct the type of therapy to be delivered (Shock if Unstable).

The stability analysis algorithm calculates R-R interval differences. These differences are calculated throughout Duration, and an average difference is also calculated. When Duration expires, rhythm stability is evaluated by comparing the current average difference to the programmed Stability and Shock if Unstable thresholds. If the average difference is greater than the programmed thresholds, the rhythm is declared unstable. Independent thresholds are available for the Stability (to inhibit) or Shock if Unstable functions; both cannot be programmed in the same zone. Programmable values for Stability Analysis can be Off or 6-120 ms.

In one embodiment, the pulse generator performs stability calculations for all episodes (even when Stability is programmed Off) and stores the results in therapy history. This stored data is useful in selecting an appropriate stability threshold.

The Stability parameter can be used to identify rapid rhythms originating in the atrium, such as atrial fibrillation, that may result in unstable rhythms in the ventricle whose rate exceeds the lowest rate threshold and which should not be treated. If a rhythm is declared stable when Duration expires, programmed therapy will be delivered. If the rhythm is declared unstable, the parameter will render a decision to withhold therapy. This is intended for rhythms originating in the atrium that may result in unstable rhythms in the ventricle whose rate exceeds the lowest rate threshold. At the end of initial Duration, if a tachycardia is declared unstable and therapy is inhibited, the pulse generator continues to evaluate for stability on each new detected interval. It will evaluate for stability as long as the zone's detection window remains satisfied, or until the V Rate>A Rate declares the ventricular rate greater than the atrial rate, or the Sustained Rate Duration (SRD) timer has expired (if programmed On). If the rate becomes stable before V Rate>A Rate is True or the SRD timer has expired, the programmed therapy is initiated immediately.

In one embodiment, Stability can be inhibited only in the lowest zone of a two- or three-zone configuration; it may be used in conjunction with other detection enhancements.

In one embodiment, Stability can be programmed to Shock If Unstable. In this programming mode, the stability analysis helps determine if ATP therapy should be bypassed in preference for the first programmed shock therapy (which may be low or high energy) for the zone. Dynamic ventricular arrhythmias such as polymorphic VT or VF may be sensed at a rate lower than the highest rate threshold and can be classified as unstable. Since the sensed rhythm may be detected in a lower zone in which ATP may be programmed, the stability analysis may be used to skip over the programmed ATP therapies and instead provide shocks to the patient. Stability is evaluated on each detection/redetection cycle, including evaluation between bursts of an ATP scheme. Once a shock has been delivered in an episode, the Shock If Unstable function no longer affects therapy selection.

The Shock If Unstable feature may be used only in the VT zone of a two-zone configuration or three-zone configuration. It cannot be programmed in a two-zone configuration if Stability or Onset is already programmed On, or if Post-shock Stability or AFib Rate Threshold is programmed On.

When Stability is programmed to inhibit, it may be combined with the Onset parameter to provide even greater specificity in characterizing arrhythmias. The enhancements can be programmed such that to initiate therapy, both Onset And Stability must indicate to treat, or such that if either Onset Or Stability indicates to treat, therapy is delivered (see FIGS. 7 and 8 for representative Onset, Stability and AFib Rate combinations and the suggested therapy).

If the combination programmed is Onset And Stability, therapy is inhibited if either parameter indicates that therapy should be withheld; that is, the rhythm is gradual Or unstable (the And condition to treat is not satisfied). If the combination programmed is Onset Or Stability, therapy is inhibited immediately at the end of Duration only if both parameters indicate that therapy should be withheld; that is, the rhythm is gradual and unstable (the Or condition to treat is not satisfied). In either case, therapy is initiated only if the And/Or conditions to treat are satisfied. When these two combinations (And/Or) are used in conjunction with Sustained Rate Duration (SRD), and the And/Or conditions are not satisfied, therapy is inhibited until V Rate>A Rate is True or SRD times out.

Figure 9:
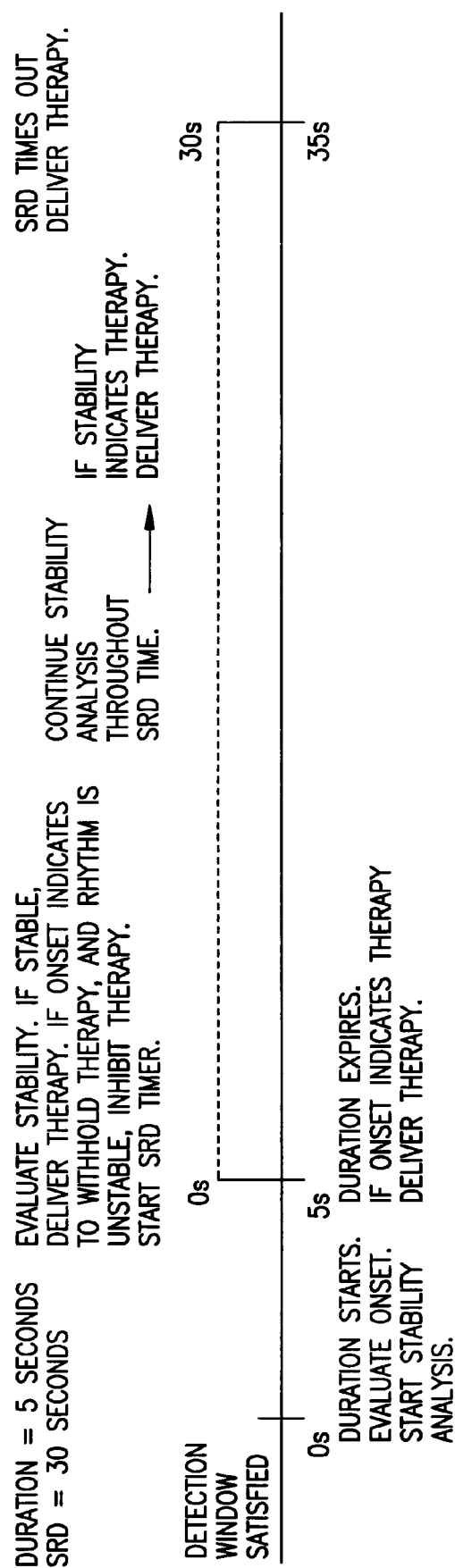
FIG. 9 illustrates Sustained Rate Duration in relation to inhibitor enhancements.

Sustained Rate Duration (SRD) allows the programmed therapy to be delivered when a tachycardia is sustained for a programmed period of time beyond Duration, but the programmed therapy inhibitors (AFib Rate Threshold, Onset, and/or Stability) indicates to withhold therapy. FIG. 9 illustrates SRD in relation to the inhibitor enhancements. It is not used in conjunction with Shock If Unstable. In one embodiment, programmable values for SRD are Off or 10 to 60 seconds.

SRD is used only when an inhibitor enhancement is programmed On. If an inhibitor is withholding therapy delivery and the Rate criterion in the lowest zone is maintained, the SRD timer begins at the end of Duration. If the detection window in the lowest zone is maintained for the programmed SRD period, the programmed therapy will be delivered at the end of the SRD period. If the rate accelerates to a higher zone and the Duration for the higher zone expires, therapy is initiated in that zone without waiting for SRD to time out. If SRD is programmed Off, an SRD timer will not start when Duration expires.

In one embodiment, detection enhancements are available in only certain zones of a multi-zone configuration. One such embodiment is shown in FIG. 5.

Figure 4:
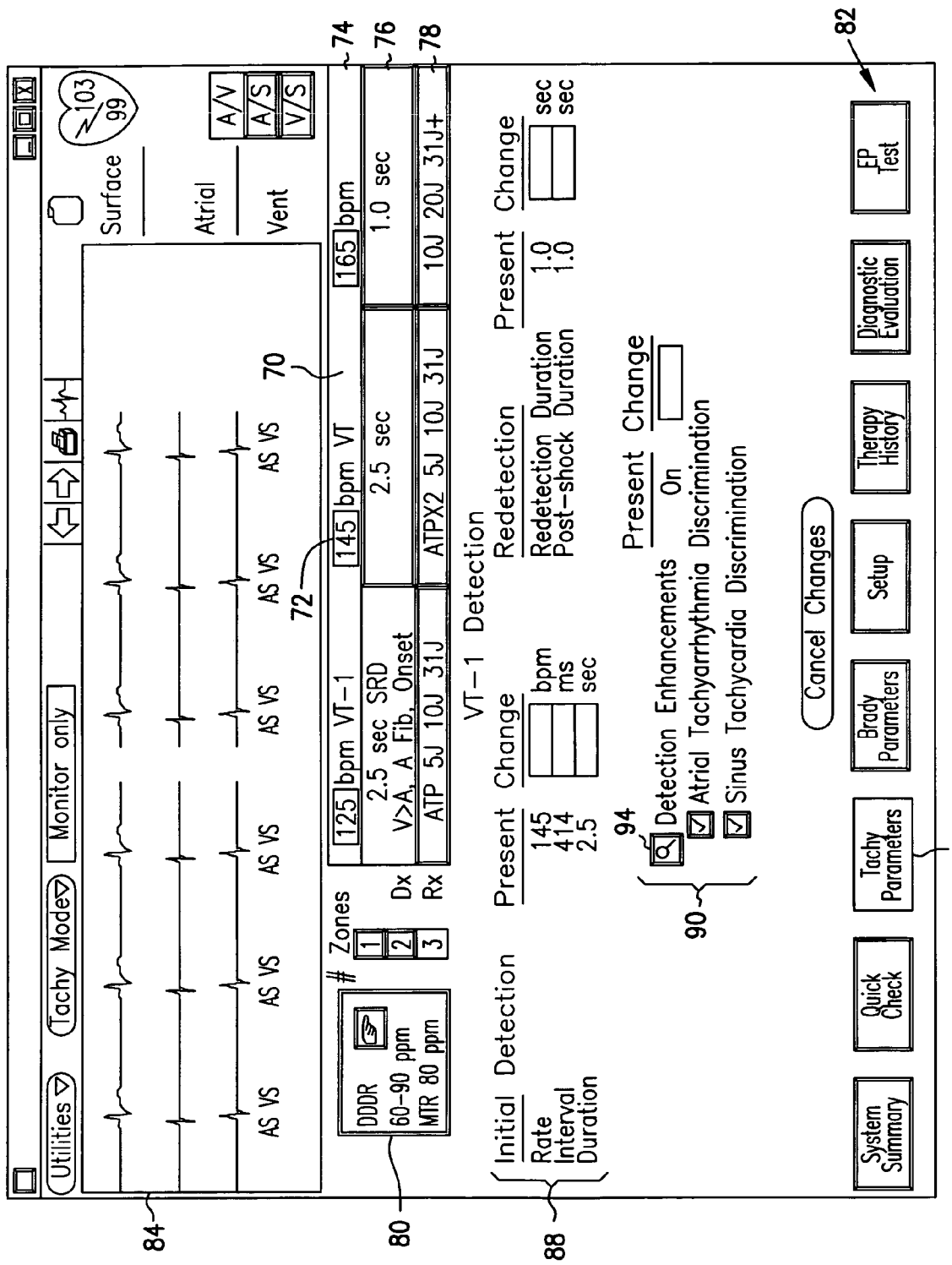
FIG. 4 illustrates display showing a representative three zone configuration.

A representative three zone configuration is shown in FIG. 4. In the embodiment shown in FIG. 4, system 10 includes up to three tachyarrhythmia zones (labeled as VT-1, VT, and VF). In one such embodiment, such as is shown in FIG. 4, each zone is identified on display 24 with its label 70 and its rate threshold 72. In the embodiment shown in FIG. 4, label 70 and its associated rate threshold 72 are displayed within a zone rate bar 74. In addition, a detection summary for each zone is displayed within detection button 76 for that zone and a therapy summary for each zone is displayed within therapy button 78 for that zone.

In one embodiment, the user accesses the detection parameters for a zone by selecting the respective detection button 76 and accesses the therapy parameters for a zone by selecting the respective therapy button 78. The user selects the rate threshold value in order to change the rate threshold for that zone. And the number of zones tachyarrhythmia zones can be modified by selecting one of the number buttons beneath the "# Zones" label.

In one embodiment, if parameter settings have changed but have not yet been programmed into the pulse generator, hatch marks (////) will appear in the summary area. When the values are programmed, the hatch marks disappear.

A subset of zone configuration information is displayed when the system summary and quick check screens are visible, which allows a shortcut to the detection and/or therapy parameters screens. (Only presently programmed values are displayed; it does not display changed data that has not yet been programmed into the device nor hatch marks.) In one embodiment, the user selects a shortcut icon to navigate to the Tachy Parameters screen, which displays detailed information. If a shortcut icon appears dim, it indicates that a change to the number of zones has not been programmed; thus a shortcut is not available to the parameter screens.

A brady therapy summary 80 is also visible in FIG. 4. This area displays the normal and post-shock bradycardia modes and rates. Additional bradycardia parameter settings may be viewed and changed by selecting the brady summary button when a shortcut icon is visible, or the Brady Parameters tool. Depending on which toolbox screen is visible, this summary button may show just the rate/zone bar or may include additional information as is shown in FIG. 4.

Toolbox 82 displays various features depending on the chosen toolbox button. The features allow interaction with the pulse generator as well as a review of data in pulse generator memory. Only one tool may be selected at a time. (In one embodiment, the System Summary tool is selected when the application is initially accessed. However, if an episode is in progress at initial interrogation, the EP Test screen will be displayed.)

In the embodiment shown in FIG. 4, windows contain information relevant to a particular function. They may include names of pulse generator parameters and functions, value boxes to accommodate value changes, buttons to open additional windows, and buttons to cancel changes or close the window. To remove the window from the display, select the button that initiates activity or select the Close or Cancel button.

Message windows are used to provide feedback during communication sessions. Some require action as indicated in the window before continuing the session, while others simply relay information without requiring further action or show status of an activity. Many message windows have a Cancel or Close button; select the desired button to cancel the action being performed as explained in the message and/or close the window.

In the embodiment shown in FIG. 4, ECG display 84 is always visible. ECG display 84 shows real-time surface ECG traces, as well as real-time electrograms (EGMs) and event markers, which are useful in ascertaining system performance. In one such embodiment, a 20-second snapshot of the ECG trace, electrograms, and markers can be printed automatically; when the cursor is positioned over the ECG display the cursor changes to a camera icon; click the left trackball key to "capture" the trace. The printed trace shows 10 seconds before and 10 seconds after the moment of command.

In one embodiment, annotated event markers identify certain intrinsic cardiac and device-related events, and provide information such as sensed/paced events, decision of detection criteria, and therapy delivery. The markers are displayed on ECG display 84.

In one embodiment, real-time electrograms can be transmitted from the pace/sense or shocking electrodes to evaluate lead system integrity such as lead fractures, insulation breaks, or dislodgments.

The number of zones, the zones' rate thresholds, and values for detection, redetection, and detection enhancement parameters can be programmed from the Zone Configuration display in FIG. 4 in the following manner.

Figure 15:
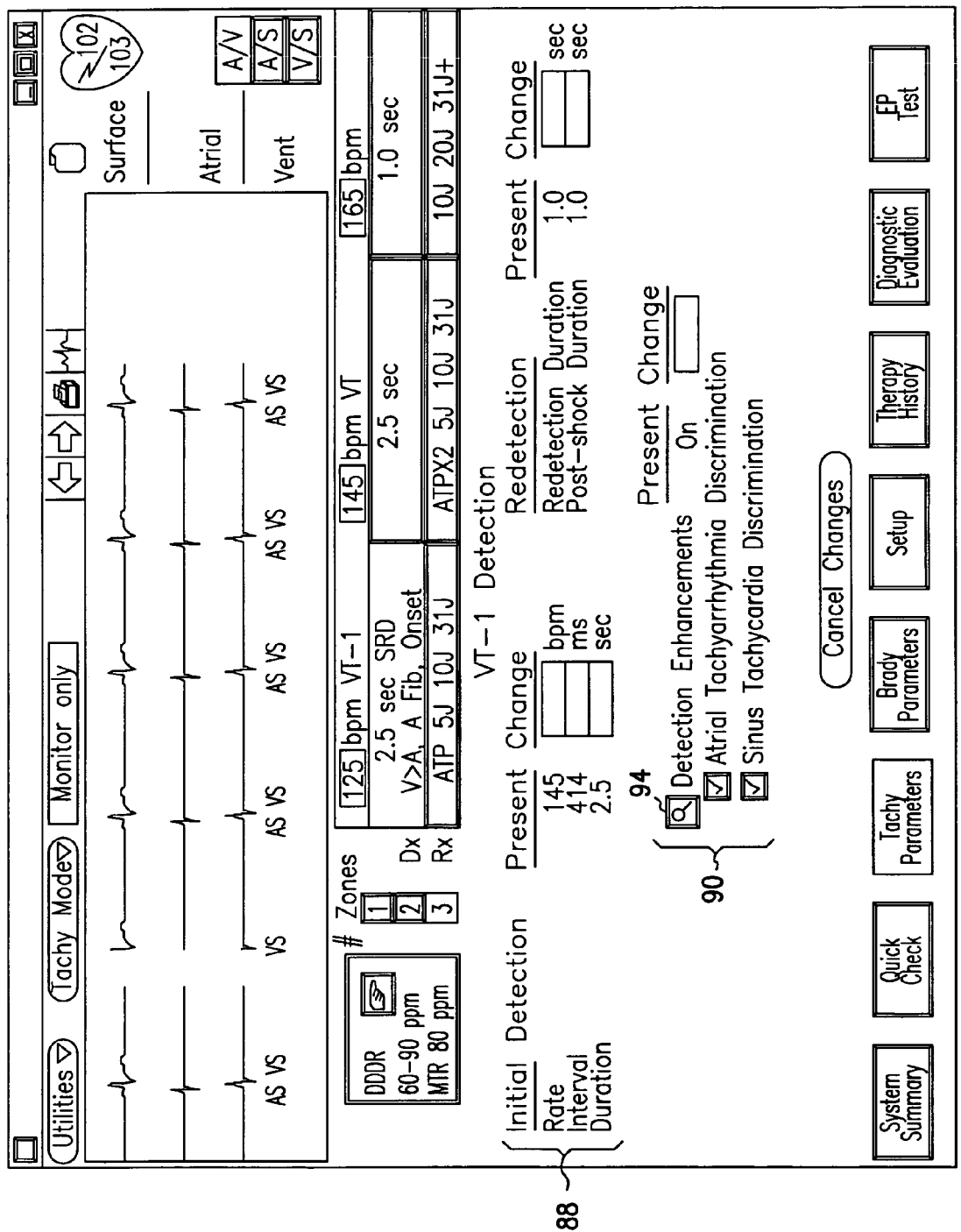
FIG. 15 illustrates a display emphasizing VT zone parameters within a multi-zone configuration.

First, select Tachy Parameters button 86 from toolbox 82 to display the zone configuration area and the selected zone's parameters. Next, change the number of zones by selecting the desired number (1, 2, or 3) from the #Zones column. The zone configuration will display the selected number of zones with hatch marks overlaying the new zones, which have not been programmed into the device yet. Third, change the rate threshold using either select box 72 from zone/rate bar 74 or via the zone's detection button 76. If a zone's detection button 76 has been selected, the initial and redetection parameters 88 are displayed. FIG. 4 illustrates the initial and redetection parameters associated with the VT-1 zone, while FIG. 15 illustrates the initial and redetection parameters associated with the VT zone. Detection enhancement rhythm discrimination categories 90 (see FIGS. 4 and 15) are displayed as well for those zones in which enhancements are available.

Next, change any of the desired initial or redetection parameters. In one embodiment, hatch marks overlay the zone's detection button 76 until the changed parameters have been programmed into the pulse generator. Note: As parameter values are changed, the information icon and/or stop sign icon may appear at the top of the main application screen to inform of potential parameter interactions. Modify parameters as required to get around these objections. More information on parameter interaction can be found in "System and Method for Detecting and Displaying Parameter Interactions," filed herewith.

Figure 16:
FIG. 16 illustrates detection enhancement details for VT zone.

Next, select the magnifying-glass icon or display enhancement parameter details. Detection enhancement details for VT-1 zone are shown in FIGS. 4, 10 and 14 Detection enhancement details for VT zone are shown in FIGS. 15 and 16.

As noted above, detection enhancement parameters can be more easily programmed by identifying the type of rhythm discrimination desired and associating the clinical rhythms with particular detection enhancements. In one embodiment, the types of clinical rhythms include: atrial tachyarrhythmia, sinus tachycardia, and polymorphic VT. FIG. 11 illustrates rhythm discrimination available per zone in multi-zone configurations.

When a rhythm discrimination is selected, preselected values are displayed for the parameters that are suitable for discriminating that rhythm (see FIGS. 12 and 13). From a zone's detection screen, detection parameters can be turned On by selecting the Detection Enhancements On or Off value box, or by selecting the individual rhythm types (see FIGS. 10, 14 and 16).

To access the detection enhancement parameters, one would select the value box in the Change column next to the text "Detection Enhancements" in a zone's detection window. If Select On is chosen, the boxes next to the type of rhythm discriminations will be checked. In Select Off is chosen, the boxes remain unchecked.

One can select individual discrimination types. To select or deselect individual discrimination types, select the box next to the discrimination type to check or uncheck the box.

One can also view detection enhancement window 92 shown in FIGS. 10, 14 and 16. In one embodiment, detection enhancement windows 92 can be viewed by selecting magnifying-glass icon 94 of FIGS. 4 and 15. The respective individual parameters and values are displayed for whichever discrimination type is selected. Parameter values can then be adjusted from this window. The discrimination types are automatically checked and unchecked according to the changes made in the enhancement window.

Window 92 is closed when the parameters values are as desired.

Figure 17:
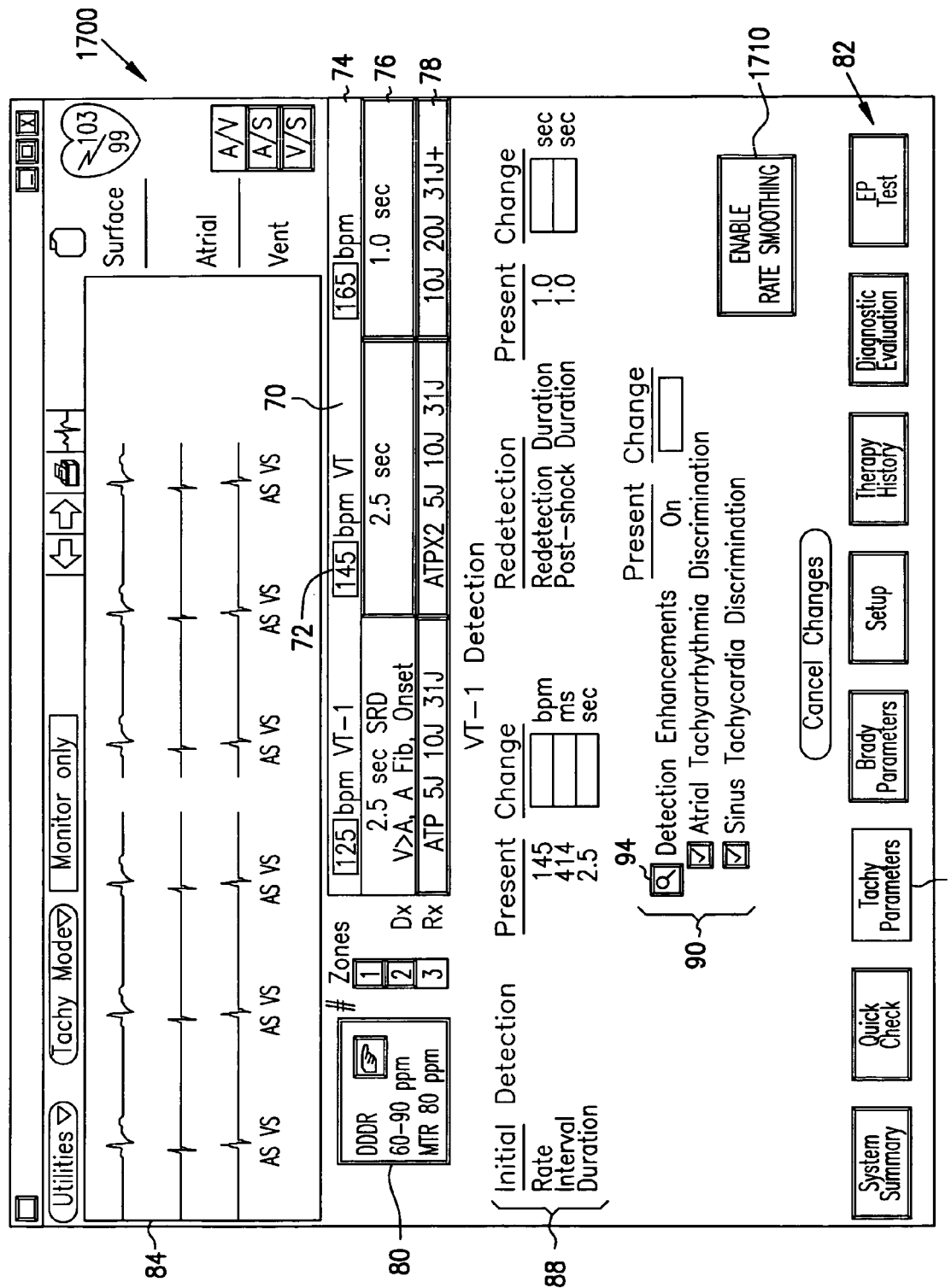
FIG. 17 illustrates one embodiment of a display.

FIG. 17 shows a programming screen 1700 with a button 1710 for enabling rate smoothing. One example of a rate smoothing algorithm and system is provided in U.S. Pat. No. 4,562,841 entitled: Programmable Multi-mode Cardiac Pacemaker, by Brockway et al., issued Jan. 7, 1986, and which is hereby incorporated by reference in its entirety. The rate smoothing function prevents the rate interval from changing by more than a predetermined percentage on a cycle-to-cycle basis.

Some patients favor devices executing a rate smoothing algorithm, because regulation of the ventricular pacing rate seems to provide more comfortable pacing. Furthermore, rate smoothing is believed to reduce the amount of ventricular tachycardia and ventricular fibrillation episodes by elimination of short-long-short induction sequences.

Toolbox 82 displays various features depending on the chosen toolbox button. The features allow interaction with the pulse generator as well as a review of data in pulse generator memory. In the embodiment shown in FIG. 17, windows contain information relevant to a particular function. They may include names of pulse generator parameters and functions, value boxes to accommodate value changes, buttons to open additional windows, and buttons to cancel changes or close the window. To remove the window from the display, select the button that initiates activity or select the Close or Cancel button.

In one embodiment of the present programming system, the screen 1700 including the button 1710 for enabling rate smoothing is available for selection by the user. In one embodiment, the rate smoothing button 1710 toggles between enabling and disabling of rate smoothing. For example, initially, when rate smoothing is disabled, the button 1710 reads "enable rate smoothing." Upon depressing the button with a mouse or other pointing device, the programmer sends a signal initiating rate smoothing in the implantable device. Once the rate smoothing function is programmed, the software operating on the programmer changes the button 1710 to read "disabled rate smoothing." If the user of the programmer presses the button it will send a signal to the programmable device to disable rate smoothing. The button 1710 will then be updated to read "enable rate smoothing."

Figure 18:
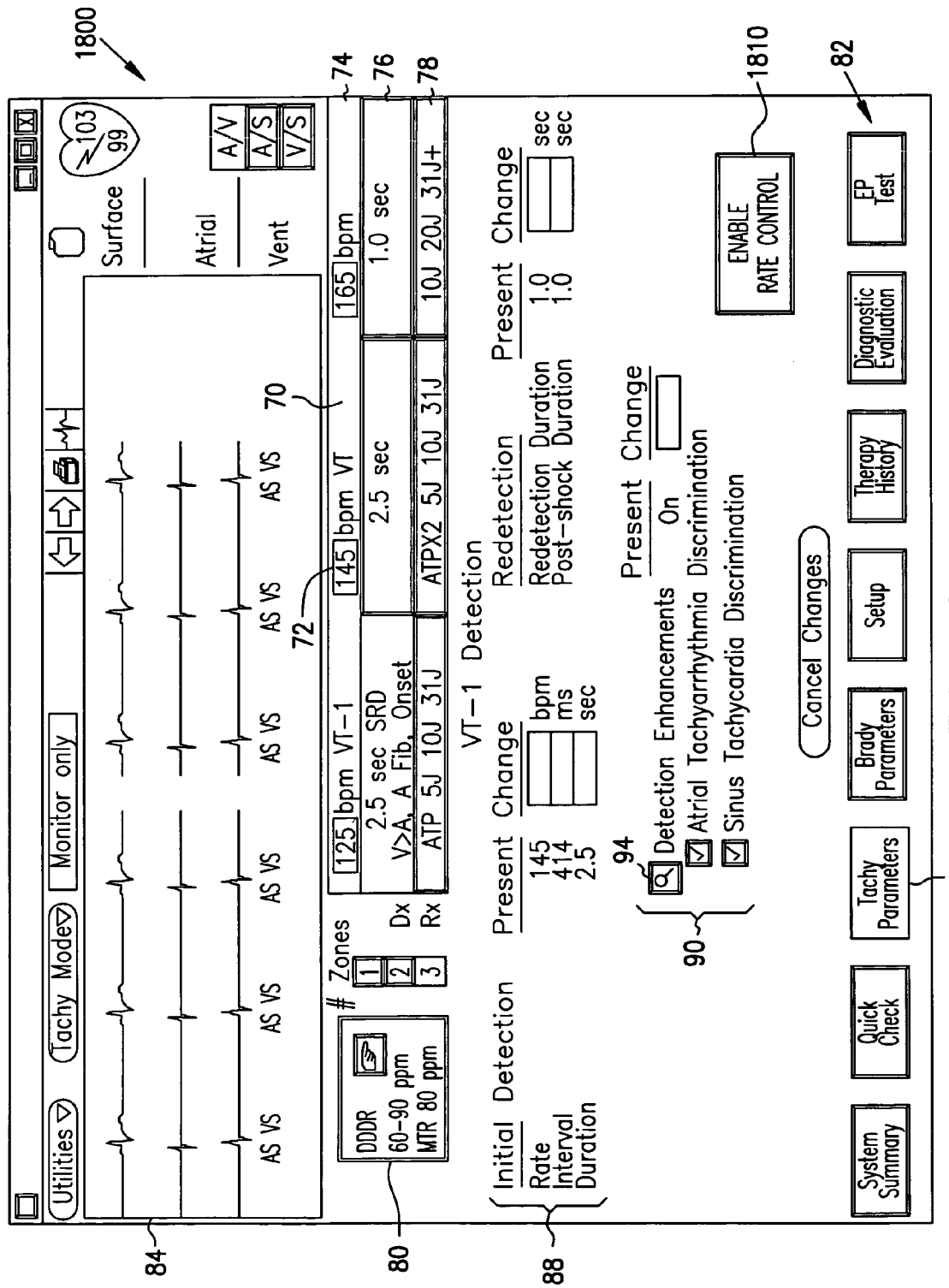
FIG. 18 illustrates one embodiment of a display.

FIG. 18 shows another embodiment of a programming screen 1800 of the present programming system, where a single "enable rate control" button 1810 selects a number of different parameters to assist the doctor in programming the device for rate control in a straightforward and efficacious manner. For example, in one embodiment, selecting the rate control button 1810 enables the following features of the programmable pulse generator:
 rate smoothing;
 atrial tachycardia response; and
 atrial flutter response.

In one embodiment, default parameter values are provided for each feature, where any number of values can be used for up-smoothing and down-smoothing. For example, for up-smoothing, the rate interval change can be 25 percent, while for down-smoothing the rate interval change can be set from 9 to 12 percent. In one embodiment, selecting the "enable rate control" button 1810 selects the following parameter values:
 rate smoothing:
  For up-smoothing a rate interval change of 25 percent percentage and a rate interval change for down-smoothing of six (6) to nine (9) percent of the previous interval.
 atrial tachy response (ATR):
  4 entry count;
  4 exit count;
  8 duration;
  70 fall-back rate;
  DDIR mode;
 atrial flutter response (AFR):
  170 beats per minute; and
 rate threshold:
  170 beats per minute.

In this embodiment, the atrial flutter response is set to the same value as a rate threshold (170 beats per minute) so that the device will obtain immediate disassociation with one fast atrial beat without a complete mode switch until it is necessary and sustained. The exemplary parameter values listed above may be varied without departing from the scope of the present invention.

A shock therapy system such as system 10 provides the ease of use of selecting detection enhancements as a function of clinical rhythm while, at the same time, providing layers of complexity, so that for those that are used to programming the specific parameters can do so. Newer users benefit from the expertise of the designers by letting the underlying expert systems set the appropriate parameters. Experienced users benefit by only having to modify the entries that differ from those preset by the expert system.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

What is claimed is:

1. A programmer for communicating to an implantable medical device, the programmer comprising:
   a programmer screen including a button adapted to enable or disable a rate control feature of the implantable medical device;
   a selection module adapted to display a plurality of predetermined clinical rhythms on the programmer screen and to allow a selection of a clinical rhythm from the plurality of predetermined clinical rhythms, the predetermined clinical rhythms each associated with one or more detection enhancements of a plurality of predetermined detection enhancements; and
   a communication module adapted to program the implantable medical device to enable or disable the rate control feature and to program the implantable medical device to enable the one or more detection enhancements associated with the selected clinical rhythm.

2. The programmer of claim 1, wherein the button is adapted to enable or disable a rate smoothing feature.

3. The programmer of claim 1, wherein the button is adapted to enable or disable an atrial tachycardia response feature.

4. The programmer of claim 1, wherein the button is adapted to enable or disable an atrial flutter response feature.

5. The programmer of claim 1, further comprising a parameter modification module adapted to store parameters related to the one or more detection enhancements associated with the selected clinical rhythm, and wherein the programmer screen is adapted to display a detection enhancement window adapted to display and allow adjustment of values of the parameters.

6. The programmer of claim 5, wherein the programming screen comprises one or more toolbox buttons each having a topic and adapted to cause the programming screen to display features related to the topic.

7. The programmer of claim 1, wherein the programmer screen comprises:
   a zone rate bar presenting a plurality of predetermined arrhythmia zones each associated with one or more detection enhancements of the plurality of predetermined detection enhancements;
   detection buttons each associated with one arrhythmia zone of the plurality of predetermined arrhythmia zones and adapted to allow display of a detection parameter summary for that one arrhythmia zone and access to the detection parameters for that one arrhythmia zone; and
   therapy buttons each associated with one arrhythmia zone of the plurality of predetermined arrhythmia zones and adapted to allow display of a therapy parameter summary for that one arrhythmia zone and access to the therapy parameters for that one arrhythmia zone.

8. The programmer of claim 7, wherein the zone rate bar comprises a zone rate bar presenting a plurality of tachyarrhythmia zones, and wherein the programmer screen further comprises a brady therapy summary adapted to present bradycardia therapy parameters and to allow access to the bradycardia therapy parameters.

9. The programmer of claim 8, wherein the zone rate bar comprises labels each representing one tachyarrhythmia zone of the plurality of tachyarrhythmia zones.

10. The programmer of claim 9, wherein the zone rate bar comprises changeable rate threshold values each associated with one tachyarrhythmia zone of the plurality of tachyarrhythmia zones.

11. A method for operating a programmer communicating with an implantable medical device, the method comprising:
   displaying a button to allow for enabling of a rate control feature of the implantable medical device;
   programming the implantable medical device to enable the rate control feature if the button is pressed when displayed to allow for the enabling of the rate control feature;
   displaying a plurality of predetermined clinical rhythms for selection;
   receiving a clinical rhythm selected from the displayed plurality of predetermined clinical rhythms;
   identifying one or more detection enhancements associated with the selected clinical rhythm;
   programming the detection enhancement parameters into the implantable medical device to perform the identified one or more detection enhancements.

12. The method of claim 11, further comprising:
   displaying the button to allow for disabling of the rate control feature if the rate control feature is enabled; and
   programming the implantable medical device to disable the rate control feature if the button is pressed when displayed to allow for the disabling of the rate control feature.

13. The method of claim 12, wherein the rate control feature comprises a rate smoothing feature.

14. The method of claim 12, wherein the rate control feature comprises an atrial tachycardia response feature.

15. The method of claim 12, wherein the rate control feature comprises an atrial flutter response feature.

16. The method of claim 12, wherein programming the detection enhancement parameters into the implantable medical device to perform the identified one or more detection enhancements comprises:
   setting detection enhancement parameters associated with the identified one or more detection enhancements; and
   programming the detection enhancement parameters into the implantable medical device to perform the identified one or more detection enhancements.

17. The method of claim 16, wherein setting the detection enhancement parameters comprises setting the detection enhancement parameters to detection enhancement parameter values stored in the programmer.

18. The method of claim 16, wherein setting the detection enhancement parameters comprises determining whether to receive a modification to the detection enhancement parameters through a user interface of the programmer.

19. The method of claim 16, wherein programming the detection enhancement parameters into the implantable medical device comprises programming the detection enhancement parameters into a defibrillator to perform at least one of delaying a delivery of a shock, inhibiting the delivery of the shock, bypassing an inhibition of the delivery of the shock, and bypassing another therapy in favor of the delivery of the shock.

20. The method of claim 16, wherein displaying the plurality of predetermined clinical rhythms comprises displaying one or more of atrial tachyarrhythmia, sinus tachycardia, polymorphic ventricular tachyarrhythmia, and ventricular fibrillation.

* * * * *

UNITED STATES PATENT AND TRADEMARK OFFICE
CERTIFICATE OF CORRECTION

PATENT NO. : 7,606,620 B2  
APPLICATION NO. : 11/369142  
DATED : October 20, 2009  
INVENTOR(S) : Gilkerson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 800 days.

Signed and Sealed this

Twelfth Day of October, 2010

David J. Kappos
*Director of the United States Patent and Trademark Office*